Figure 1:
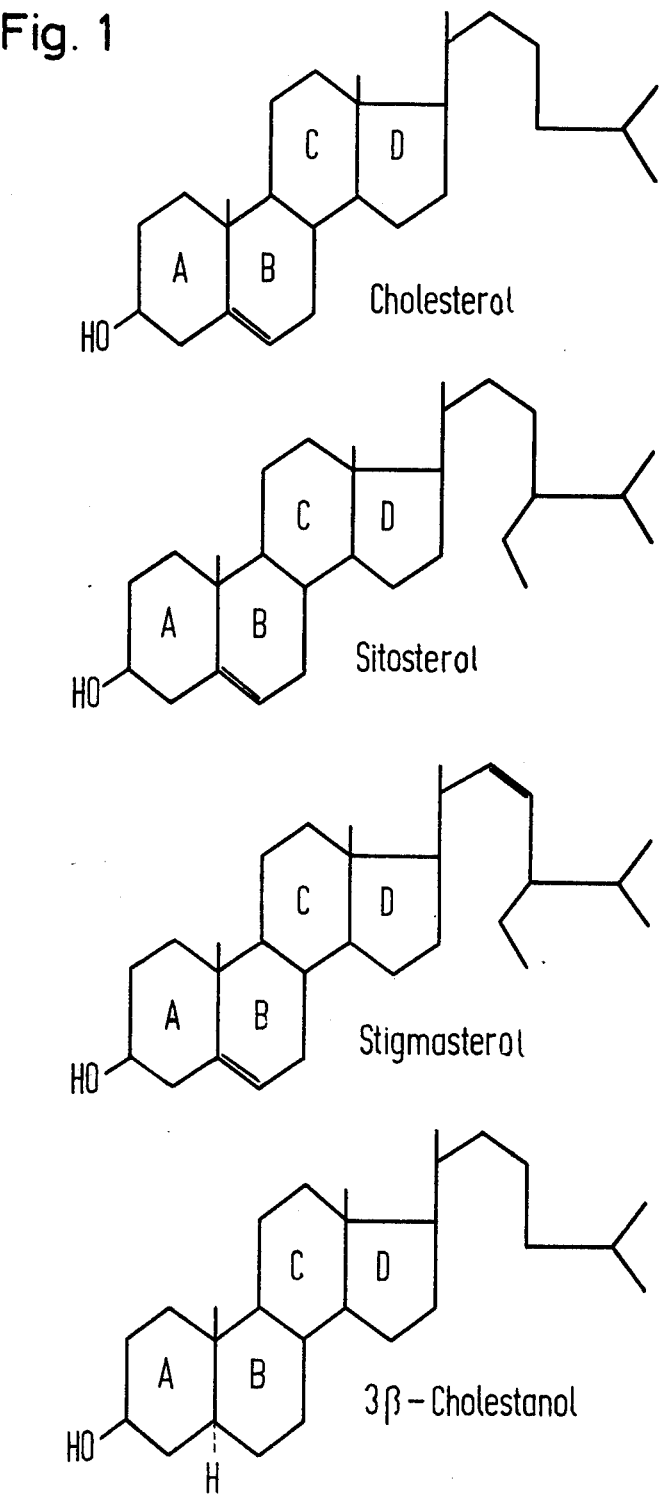

United States Patent

Gruber et al.

[11] 4,008,127
[45] Feb. 15, 1977

[54] PROCESS FOR THE PREPARATION OF CHOLESTEROL OXIDASE

[75] Inventors: Wolfgang Gruber, Tutzing-Unterzeismering; Hans Ulrich Bergmeyer, Tutzing, Upper Bavaria; Michael Nelboeck-Hochstetter, Tutzing, Upper Bavaria; Klaus Beaucamp, Tutzing, Upper Bavaria; Günter Holz, Aichach; Johanna Gramsall; Günter Lang, both of Tutzing, Upper Bavaria, all of Germany

[73] Assignee: Boehringer Mannheim GmbH, Mannheim-Waldhof, Germany

[22] Filed: Nov. 20, 1975

[21] Appl. No.: 633,997

[30] Foreign Application Priority Data

Nov. 29, 1974 Germany .................. 2456586

[52] U.S. Cl. .................................................. 195/65
[51] Int. Cl.² ........................................ C12D 13/10
[58] Field of Search ....... 195/62, 65, 66 R, 103.5 R

[56] References Cited

UNITED STATES PATENTS 3,907,642  9/1975  Richmond .................. 195/62
3,909,359  9/1975  Goodhue et al. .......... 195/65

FOREIGN PATENTS OR APPLICATIONS 1,391,876  4/1975  United Kingdom

Primary Examiner—Lionel M. Shapiro
Attorney, Agent, or Firm—Burgess, Dinklage & Sprung

[57] ABSTRACT

Cholesterol oxidase which oxidizes cholesterol with oxygen to give cholestenone and hydrogen peroxide, is prepared by culturing *Nocardia erthropolis* ATCC 17895, *Nocardia erthropolis* ATCC 4277, *Nocardia formica* ATCC 14811 or *Proactinomyces erythropolis* NCIB 9158 first on a peptone-containing mineral salt medium and thereafter on at least one sterol compound as the sole source of carbon, and then isolating the cholesterol oxidase formed from the cultured microorganism, wherein said sterol compound is of the formula

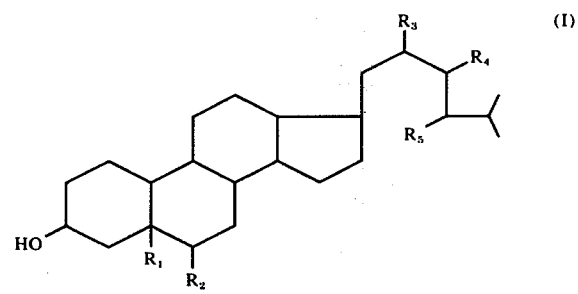

in which
$R_1$ and $R_2$ are hydrogen or together represent a double bond,
$R_3$ and $R_4$ are hydrogen or together represent a double bond, and
$R_5$ is hydrogen or alkyl containing up to 3 carbon atoms.

14 Claims, 2 Drawing Figures

Cholesterol

Sitosterol

Stigmasterol

3β-Cholestanol

Ergosterol (Provitamin $D_2$)

$\Delta$ 7-Dehydro-Cholesterol $\Delta$ 4-Cholestenol $\Delta$ 4-Cholestenone

PROCESS FOR THE PREPARATION OF CHOLESTEROL OXIDASE

The present invention is concerned with a process for obtaining cholesterol oxidase, which oxidizes cholesterol with oxygen to give cholestenone and hydrogen peroxide.

Our British Patent Specification No. 1,391,876 discloses the use of *Nocardia erythropolis* ATCC 17895, *Nocardia erythropolis* ATCC 4277, *Nocardia formica* ATCC 14811 and *Proactinomyces erythropolis* NCIB 9158 for obtaining cholesterol oxidase. According to this British Patent Specification, cholesterol is preferably used as the source of carbon for culturing of the above-mentioned micro-organisms.

Surprisingly, we have now found that results which are just as good as or, in some cases, are even superior thereto are achieved when the above-mentioned micro-organisms are cultured on certain other sterols instead of on cholesterol, in accordance with the present invention.

The present invention provides a process for obtaining cholesterol oxidase, which catalyzes the oxidation of cholesterol according to the following equation:

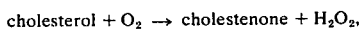

comprising culturing *Nocardia erythropolis* ATCC 17895, *Nocardia erythropolis* ATCC 4277, *Nocardia formica* ATCC 14811 or *Proactinomyces erythropolis* NCIB 9158 first on a peptone-containing mineral salt medium and thereafter on at least one sterol compound as the sole source of carbon, and then isolating the cholesterol oxidase formed from the cultured micro-organisms.

The sterol compound used in the invention is of the formula:

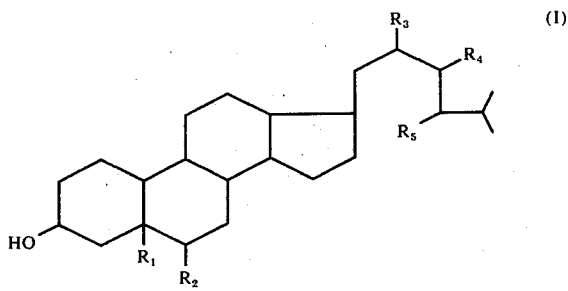

in which
$R_1$ and $R_2$ are hydrogen or together represent a double bond,
$R_3$ and $R_4$ are hydrogen or together represent a double bond, and
$R_5$ is hydrogen or alkyl containing up to 3 carbon atoms.

Figure 2:
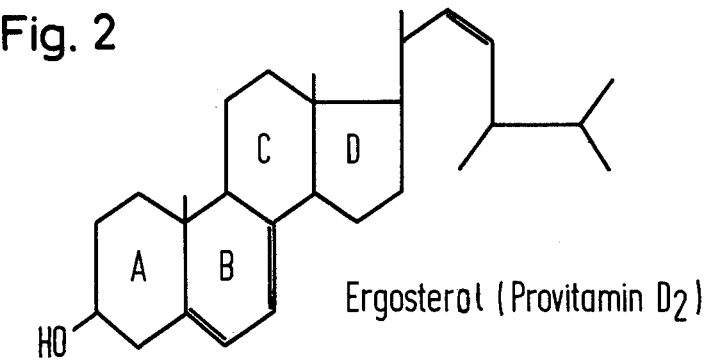
Figure 2:
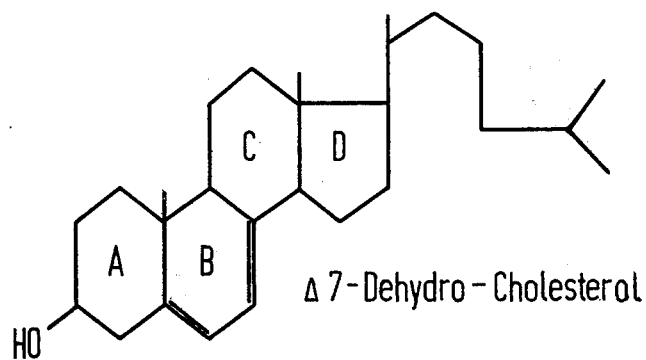
Figure 2:
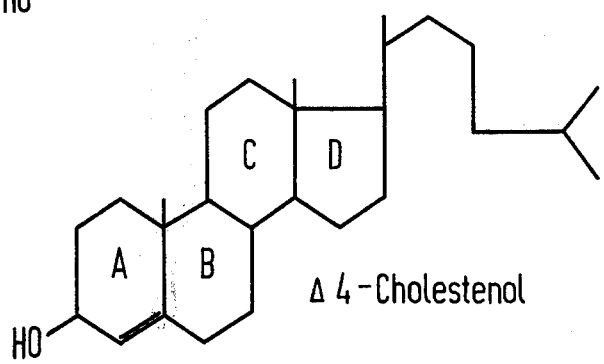
Figure 2:
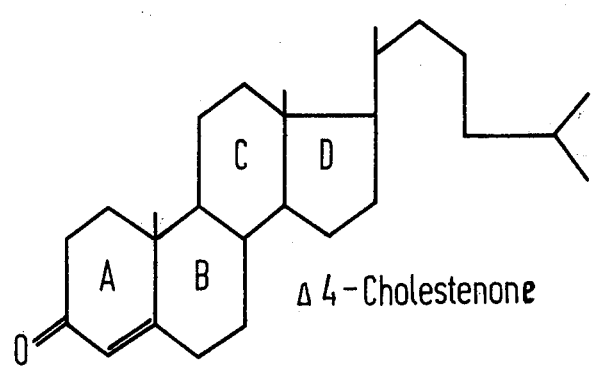

Specific examples of sterols which can be used according to the present invention include sitosterol, cholestanol and stigmasterol, the structures of which are shown in the accompanying drawings in which FIG. 1. represents the structures of cholesterol, sitosterol, stigmasterol, and 3β-cholestanol; and FIG. 2 represents the structures of ergosterol (provitamin $D_2$), Δ7-dehydro-cholesterol, Δ4-cholesterol, and Δ4-cholestenone.

Sitosterol with its ethyl side chain on the $C_{24}$ carbon atom (see FIG. 1 of the accompanying drawings) is even superior to cholesterol, whereas stigmasterol and cholestanol generally do not achieve the high effectiveness of sitosterol.

Sterols are, even, when they have a cholesterol-like structure, generally induction-inactive and are, therefore, not suitable for obtaining cholesterol oxidase-rich micro-organisms Thus, for example, ergosterol, Δ7-dehydrocholesterol, Δ4-cholesten-3β-ol and 4-cholesten-3β-one (see FIG. 2 of the accompanying drawings) prove to be induction-inactive and are thus useless for culturing cholesterol oxidase-rich micro-organisms. Therefore, it was not to have been foreseen that, with the above-mentioned special group of sterols, it would be possible to achieve a very good induction of the cholesterol oxidase formation.

The induction-active sterols to be used according to the present invention can be employed in the form of crude sterols or as mixtures with other induction-active or also induction-inactive sterols. Mixtures of this type include, for example, crude sterol mixtures which can be obtained from vegetable material, for example from maize germ extracts. Thus, by distilling certain maize extracts and recovering the distillation residues, crude sterol mixtures are obtained which contain about 50 to 70% by weight of sterols.

The above-mentioned micro-organisms can be cultured in a manner analogous to that described in our British Patent Specification No. 1,391,876. As a nutrient medium, it has proved to be useful to use an aqueous solution containing about 0.1 to 2% by weight peptone, 0.01 to 0.2% by weight dipotassium hydrogen phosphate, 0.05 to 1% by weight ammonium dihydrogen phosphate, 0.05 to 0.1% by weight magnesium sulphate heptahydrate and traces of iron chloride and calcium chloride and having a pH value between 6 and 9. The initial addition of the sterols to be used according to the present invention is preferably in an amount between 0.01 and 0.2% by weight.

Further culturing takes place in a main culture in which the micro-organisms are allowed to grow on a peptone-containing mineral salt medium and to this is added, preferably as soon as the logarithmic growth phase is reached, an aqueous emulsion which has been produced by wet grinding an aqueous suspension of the induction-active sterol or sterol mixture and subsequent heat sterilization thereof. The emulsion is thereby preferably added to the culture broth in such an amount that, in all, 1 to 3 g. of a sterol which can be used according to the present invention or 1 to 50 g. of a crude sterol mixture which can be used according to the present invention are added over the course of the growth period.

According to a preferred embodiment of the present invention, micro-organisms are used which have been cultured on a sterol of general formula (I) as the sole source of carbon in that to the micro-organisms grown on a peptone-containing mineral salt medium there is added an emulsion which has been produced by the wet grinding of an aqueous suspension of a sterol of general formula (I) and subsequent heat sterilization thereof, as soon as the logarithmic growth phase is reached, in order to obtain chloesterol oxidase.

The following Examples illustrate the present invention:

EXAMPLE 1

15 Liters of a nutrient medium, comprising 0.5% by weight peptone from casein (tryptic), 0.05% by weight dipotassium hydrogen phosphate, 0.2% by weight ammonium dihydrogen phosphate, 0.02% by weight magnesium sulfate heptahydrate and traces of iron chloride and calcium chloride in tap water and adjusted to pH 7.5 with potassium hydroxide, were inoculated in a stirrer fermentor with 500 ml. of a well grown pre-culture of *Nocardia erythropolis* ATCC 4277 and vigorously aerated, 0.05% by weight sitosterol being added initially. With the commencement of the logarithmic growth phase, recognizable by the appearance of an increase of turbidity, sterilized sitosterol yeast extract suspension, which had been prepared by wet grinding, was added in large portions in the course of the further culturing so that, within the course of 20 hours, a total of 50 g. sitosterol was introduced into the fermentor. 5 hours after the last addition, the cell mass was collected by centrifuging. 53.3 g. of dry bacterial mass was obtained. After ultra-sonic digestion, there were obtained 3 U/g. cholesterol oxidase, 1 U thereof thereby corresponding to the formation of 1 $\mu$ Mol hydrogen peroxide/minute or to the oxidation of 1 $\mu$ Mol cholesterol/minute, under the following test conditions:

2.31 ml. phosphate buffer (0.05 M, pH 7.0) containing 1 mg./m. ammonium 2,2'-azino-di-(ethyl-benzthiazoline-6-sulfonate)

0.05 ml. cholesterol solution, containing 3.7 mg. cholesterol in tert.-butanol 0.6 ml. tert.-butanol, 0.02 ml. peroxidase corresponding to 9 U, 0.02 ml. bacterial extract.

EXAMPLE 2

The experiment of Example 1 was repeated but, instead of the aqueous sitosterol yeast extract emulsion, an aqueous 3$\beta$-cholestanol yeast extract emulsion was used.

52.5 g. dry bacterial mass was obtained.

EXAMPLE 3

The experiment of Example 1 was repeated but, instead of the aqueous sitosterol yeast extract emulsion, there was used an aqueous stigmasterol yeast extract emulsion.

52.5 g. dry bacterial mass was obtained.

It will be understood that the specification and examples are illustrative but not limitative of the present invention and that other embodiments within the spirit and scope of the invention will suggest themselves to those skilled in the art.

What is claimed is:

1. Process for the preparation of cholesterol oxidase, capable of catalyzing the oxidation of cholesterol according to the equation cholesterol + $O_2$ → cholestenone + $H_2O_2$, which process comprises culturing *Norcardia erthropolis* ATCC 17895, *Nocardia erthropolis* ATCC 4277, *Nocardia formica* ATCC 14811 or *Proactinomyces erythropolis* NCIB 9158 first on a peptone-containing mineral salt medium and thereafter on at least one sterol compound as the sole source of carbon, and then isolating the cholesterol oxidase formed from the cultured micro-organisms, wherein said sterol compound is of the formula (I)

in which $R_1$ and $R_2$ are hydrogen or together represent a double bond, $R_3$ and $R_4$ are hydrogen or together represent a double bond; and $R_5$ is hydrogen or alkyl containing up to 3 carbon atoms.

2. Process as claimed in claim 1 wherein $R_1$ and $R_2$ in the formula are hydrogen.

3. Process as claimed in claim 1 wherein $R_1$ and $R_2$ in the formula represent a double bond.

4. Process as claimed in claim 1 wherein $R_3$ and $R_4$ in the formula represent hydrogen.

5. Process as claimed in claim 1 wherein $R_3$ and $R_4$ in the formula represent a double bond.

6. Process as claimed in claim 1 wherein $R_5$ in the formula is hydrogen.

7. Process as claimed in claim 1 wherein $R_5$ in the formula is alkyl of up to 3 carbon atoms.

8. Process as claimed in claim 1 wherein said sterol compound is sitosterol.

9. Process as claimed in claim 1 wherein said sterol compound is cholestanol.

10. Process as claimed in claim 1 wherein said sterol compound is stigmasterol.

11. Process as claimed in claim 1 wherein an emulsion produced by the wet grinding of an aqueous suspension of a sterol compound according to claim 1 and subsequent heat sterilization thereof, is added to the micro-organism when the logarithmic growth phase is reached.

12. Process as claimed in claim 1 wherien said cholesterol compound is added in a total amount of from 1 to 30 g. per liter of culture broth.

13. Process as claimed in claim 12 wherein said cholesterol compound is at least one of sitosterol, stigmasterol, and 3 $\beta$-cholestanol.

14. Process as claimed in claim 11 wherein said sterol compound is at least one of sitosterol, stigmasterol, and 3$\beta$-cholestanol.

* * * * *